(12) United States Patent
Sandera

(10) Patent No.: US 10,408,798 B2
(45) Date of Patent: Sep. 10, 2019

(54) SYSTEM AND METHOD FOR DETECTING STRUCTURAL DAMAGE IN A COMPONENT

(71) Applicant: HONEYWELL INTERNATIONAL INC., Morris Plains, NJ (US)

(72) Inventor: Cenek Sandera, Brno (CZ)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/479,472

(22) Filed: Apr. 5, 2017

(65) Prior Publication Data

US 2018/0292361 A1 Oct. 11, 2018

(51) Int. Cl.
*G01N 29/44* (2006.01)
*G01M 5/00* (2006.01)
(Continued)

(52) U.S. Cl.
CPC ...... *G01N 29/4427* (2013.01); *G01M 5/0016* (2013.01); *G01M 5/0033* (2013.01);
(Continued)

(58) Field of Classification Search
CPC .. G01N 29/4427; G01N 29/043; G01N 29/26; G01N 29/48; G01N 2291/0231;
(Continued)

(56) References Cited

U.S. PATENT DOCUMENTS 8,036,836 B2 10/2011 Liu et al.
8,447,530 B2 5/2013 Pado et al.
(Continued)

FOREIGN PATENT DOCUMENTS

WO 2011/106890 A1 9/2011

OTHER PUBLICATIONS

Hidden Solutions, LLC (NASA SBIR); Multi-Path Guided Wave Imaging for Inspection and Monitoring of Large, Complex Structures; Quantitative Ultrasonic Evaluation, Sensing and Testing (QUEST) Laboratory; Nov. 15, 2012.
(Continued)

*Primary Examiner* — Shahed Ahmed
(74) *Attorney, Agent, or Firm* — Lorenz & Kopf, LLP

(57) ABSTRACT

Systems and methods are provided for detecting structural damage in a component. An ultrasonic guided wave (UGW) device scans the component along a monitoring path to generate a monitoring UGW measurement and along a reference path to generate a reference UGW measurement. A database has a plurality of database reference UGW measurements each corresponding to a database monitoring UGW measurement. A damage detection module searches the database for the database reference UGW measurement that matches the reference UGW measurement. When a match is found, the damage detection module obtains the database monitoring UGW measurement corresponding to the matched database reference UGW measurement, compares the monitoring UGW measurement with the database monitoring UGW measurement, and identifies damage to the component based on the comparison. When the match is not found, the damage detection module updates the database with the reference UGW measurement and the monitoring UGW measurement.

20 Claims, 3 Drawing Sheets

(51) Int. Cl.
*G01N 29/04* (2006.01)
*G01N 29/26* (2006.01)
*G01N 29/48* (2006.01)

(52) U.S. Cl.
CPC ........ *G01M 5/0041* (2013.01); *G01M 5/0066* (2013.01); *G01M 5/0075* (2013.01); *G01N 29/043* (2013.01); *G01N 29/26* (2013.01); *G01N 29/48* (2013.01); *G01N 2291/0231* (2013.01); *G01N 2291/0234* (2013.01); *G01N 2291/0289* (2013.01); *G01N 2291/2694* (2013.01)

(58) Field of Classification Search
CPC ... G01N 2291/0234; G01N 2291/0289; G01N 2291/2694; G01M 3/26; G01M 5/0033; G01M 7/025
USPC .... 702/32, 33, 35, 39, 48, 66, 71, 104, 144, 702/171
See application file for complete search history.

(56) References Cited

U.S. PATENT DOCUMENTS

| 2006/0069520 | A1  | 3/2006  | Gorinevsky et al. |
| 2009/0326834 | A1* | 12/2009 | Sundaresan ......... G01M 5/0041 702/34 |
| 2015/0160169 | A1* | 6/2015  | Hall .................... G01N 29/04 702/39 |
| 2015/0308920 | A1* | 10/2015 | Sandera ............... G01M 7/025 702/39 |
| 2016/0091388 | A1* | 3/2016  | De Baere ........... G01M 5/0033 73/40 |
| 2016/0340058 | A1* | 11/2016 | Da Silva ............. B64D 45/00 |

OTHER PUBLICATIONS

Extended EP Search Report for Application No. 18164752.0 dated Aug. 29, 2018.

* cited by examiner

SYSTEM AND METHOD FOR DETECTING STRUCTURAL DAMAGE IN A COMPONENT

TECHNICAL FIELD

The exemplary embodiments described herein generally relate to structural health monitoring for components and more particularly to using ultrasonic guided waves to monitor structural damage to components.

BACKGROUND

Structural health monitoring (SHM) is a process of identifying damage in structures and components. Generally speaking, damage can be characterized as a change in the material or geometric properties of the structure such as weakening or physical distortion. Typically, SHM systems monitor and measure structural properties over time and compare the current results to either baseline measurements or historical measurements to determine the current health of the structure. For example, sensors in bridges can monitor the properties of the bridge components over time to identify when the bridge has become unsafe due to deterioration or an event like an earthquake.

Similar SHM systems have been employed in aircraft to monitor the airframe and various aircraft structures to help identify structural issues with aircraft components before they fail. One such technique is to use an ultrasonic guided wave (UGW) system to detect damage to various mechanical structures and components due to impacts, corrosion, and the like. Generally speaking, the UGW system transmits a signal between two points on the component and determines the health of the component based on how the signal has changed relative to a reference value. However, the signals transmitted through the component are not just impacted by the presence of structural damage, but environmental factors as well. Component temperature, loading, or age can all negatively impact the reliability of the SHM system by increasing the number of false positives or, in a worse case, masking real structural damage.

Accordingly, it is desirable to provide a system and method for detecting and identifying structural damage in a component that minimizes the impact of environmental factors on the SHM reading. Furthermore, other desirable features and characteristics of the exemplary embodiments will become apparent from the subsequent detailed description and the appended claims, taken in conjunction with the accompanying drawings and the foregoing technical field and background.

BRIEF SUMMARY

In an exemplary embodiment, a system for detecting structural damage in a component includes an ultrasonic guided wave (UGW) device. The UGW device is configured to scan the component along a monitoring path to generate a monitoring UGW measurement and further configured to scan the component along a reference path to generate a reference UGW measurement. The system further includes a database having a plurality of database reference UGW measurements each corresponding to a database monitoring UGW measurement. The system further includes a damage detection module configured to search the database for the database reference UGW measurement that matches the reference UGW measurement. When the matching database reference UGW measurement is found, the damage detection module is configured to obtain, from the database, the database monitoring UGW measurement corresponding to the matched database reference UGW measurement. The damage detection module is configured to compare the monitoring UGW measurement with the obtained database monitoring UGW measurement and identify damage to the component based on the comparison. When the matching database reference UGW measurement is not found, the damage detection module is configured to update the database with the reference UGW measurement and the monitoring UGW measurement.

In an exemplary embodiment, a method for detecting structural damage in a component includes scanning, with an ultrasonic guided wave (UGW) device, the component along a monitoring path to generate a monitoring UGW measurement. The method further includes scanning, with the UGW device, the component along a reference path to generate a reference UGW measurement, the reference path corresponding to the monitoring path. A database having a plurality of database reference UGW measurements each corresponding to a database monitoring UGW measurement is provided and the database is searched for the database reference UGW measurement that matches the reference UGW measurement. When the matching database reference UGW measurement is found, the method obtains, from the database, the database monitoring UGW measurement corresponding to the matched database reference UGW measurement, compares the monitoring UGW measurement with the obtained database monitoring UGW measurement, and identifies damage to the component based on the comparison. When the matching database reference UGW measurement is not found, the method updates the database with the reference UGW measurement and the monitoring UGW measurement.

BRIEF DESCRIPTION OF THE DRAWINGS

The present invention will hereinafter be described in conjunction with the following drawing figures, wherein like numerals denote like elements.

DETAILED DESCRIPTION

Figure 1:
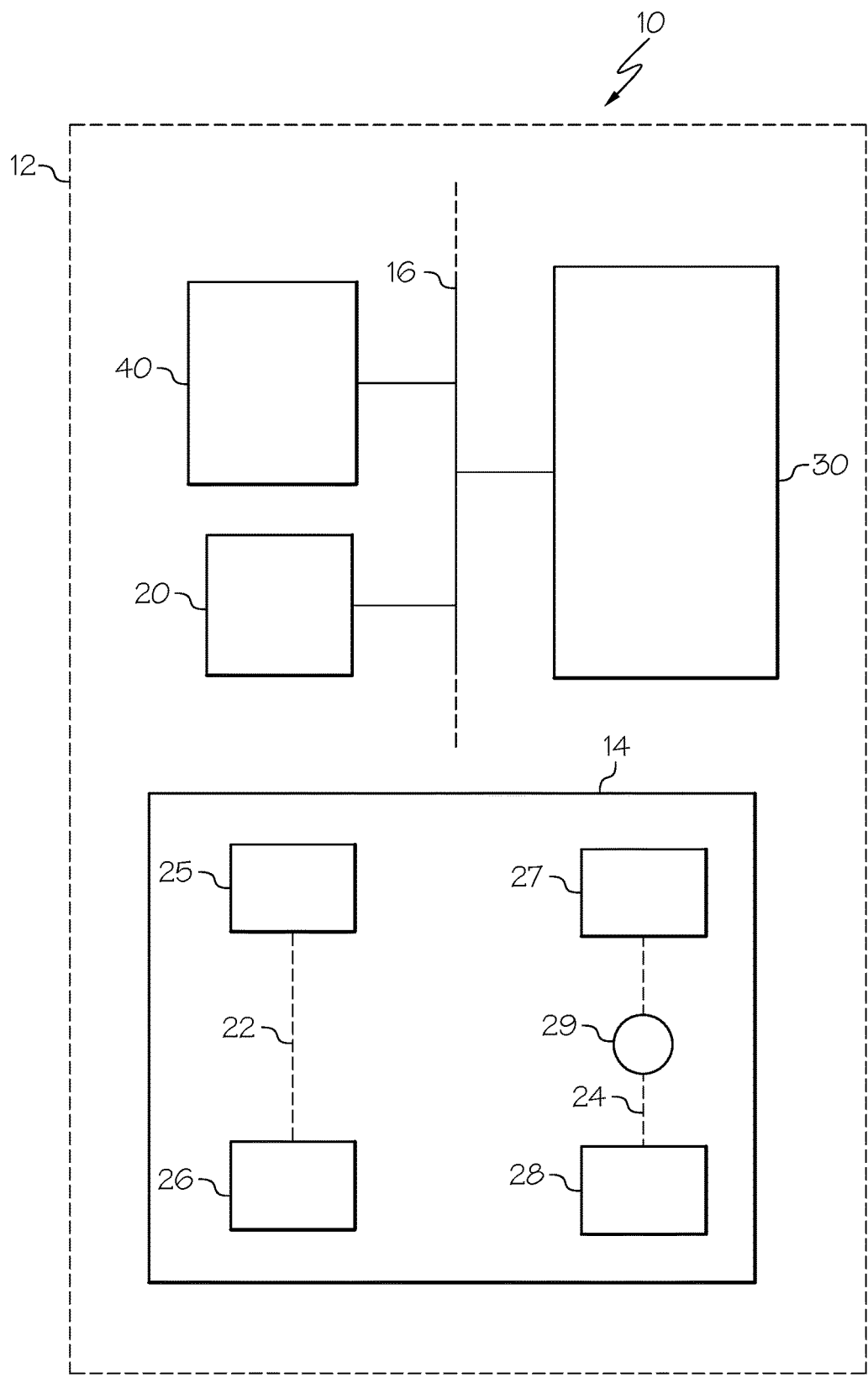
FIG. 1 is a block diagram of an exemplary system for detecting structural damage in a component.

The following detailed description is merely illustrative in nature and is not intended to limit the embodiments of the subject matter or the application and uses of such embodiments. Any implementation described herein as exemplary is not necessarily to be construed as preferred or advantageous over other implementations. Furthermore, there is no intention to be bound by any expressed or implied theory presented in the preceding technical field, background, brief summary, or the following detailed description.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The word "exemplary" is used exclusively herein to mean "serving as an example, instance, or illustration." Any embodiment described herein as "exemplary" is not necessarily to be construed as preferred or advantageous over other embodiments. Any of the above devices are exemplary, non-limiting examples of a computer readable storage medium.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal. Any of the above devices are exemplary, non-limiting examples of a computer readable storage medium In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

With reference now to FIG. 1, a system 10 for detecting structural damage in a component 14 is shown herein. The system 10 is generally implemented in an aircraft 12, however, in a non-limiting embodiment, the system 10 is implemented in other vehicles including, helicopters, automobiles, spacecraft, trains, and the like. In a non-limiting embodiment, the system 10 is temporarily connected to the aircraft component 14 and removed after use. The system 10 includes a an ultrasonic guided wave (UGW) device 20, a database 30, and a damage detection module 40.

The component 14 of the aircraft 12 is generally a structural element of the aircraft 12 such that it would be worthwhile to perform SHM upon the component 14. For example, the component 14 may be a load bearing support, a control surface, or a section of the aircraft 12 that is hard to reach an examine. In a non-limiting example, the component 14 may be metallic or a composite. The specific material type of the component 14 need only be suitable for UGW measurement by the UGW device 20 and is not intended to be limiting.

The UGW device 20 is configured to scan the component 14 along a monitoring path 24 to generate a monitoring path UGW measurement and to scan the component 14 along a reference path 22 to generate a reference UGW measurement. In a non-limiting example, the UGW device 20 is in communication with the database 30, damage detection module 40, and other various systems on the aircraft 12 (not shown) via a bus 16. Bus 16 may be a wired communication bus, a wireless communication bus, or a combination thereof.

The UGW device 20 performs SHM on the component 14 of the aircraft. Compared to other global vibrations in the component 14, UGW measurements offer increased sensitivity to smaller defects and variations in the component 14 due to the smaller wavelengths involved. The ultrasonic waves used in UGW measurement can be detected several dozen meters away from the source, depending on the component 14 being measured, making this technique suitable for aircraft 12 that include many elongated components 14, such as wings, that have internal structures that may be hard to access and routinely evaluate.

In a non-limiting example, the UGW device 20 transmits an ultrasonic signal from a first sensor 25 through the component 14. The ultrasonic signal travels from the first sensor 25 to a second sensor 26 along a reference path 22. The transmitted signal is received by the second sensor 26 as a reference UGW measurement. The reference UGW measurement captures how the component 14 impacts the ultrasonic signal as it is transmitted from the first sensor 25 to the second sensor 26. The reference UGW measurement is impacted by the component 14 itself and reflects how the component 14 behaves under the current environmental conditions. Stated differently, the shape of the reference UGW measurement is physically impacted as it is transmitted through the component 14 and is further altered based on the current environmental conditions that the component is subjected to at the time of the measurement.

Figure 2:
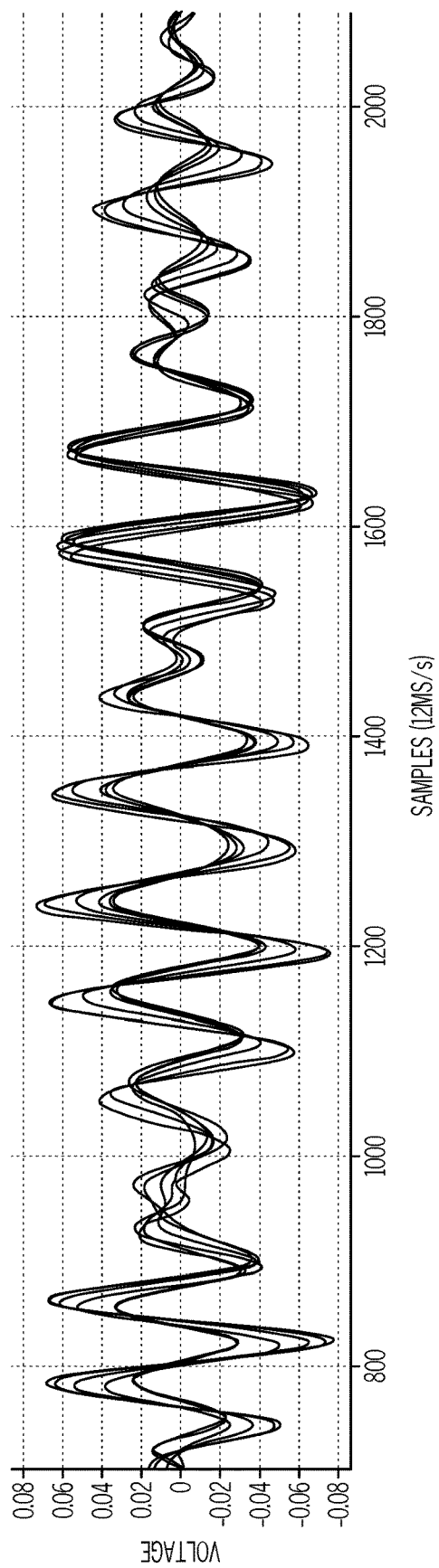
FIG. 2 is an exemplary graph of a plurality of ultrasonic guided wave measurement signals in accordance with the exemplary embodiment.

With reference now to FIG. 2 and with continued reference to FIG. 1, exemplary reference UGW measurement signals are depicted herein. The reference UGW measurement signals are for illustrative purposes only and are not intended to be limiting. As shown in FIG. 2, a plurality of reference UGW measurement signals are plotted on a common axis to depict how the reference UGW measurement signals change their physical shape or have observed geometrical change due to changes in the physical properties of the component 14. For example, the changes in the reference UGW measurement signals can manifest in a change in the amplitude of the reference UGW measurement signals or a change in the position in time of the reference UGW measurement signals. Two reference UGW measurement signals should be the same if the reference path 22 is the same and the component 14 is subjected to the same environmental conditions. The reference UGW measurement signals will differ though as the environmental conditions of the component 14 change. For example, varying environmental conditions can include a change in temperature of the component 14, a change in loading of the component 14, a change in age of the component 14, or a combination thereof.

In a non-limiting example, the UGW device 20 transmits an ultrasonic signal from a third sensor 27 through the component 14. The ultrasonic signal travels from the third sensor 27 to a fourth sensor 28 along a monitoring path 24. The transmitted signal is received by the fourth sensor 28 as a monitoring UGW measurement. Similar to the reference UGW measurement, the monitoring UGW measurement captures how the component 14 impacts the ultrasonic signal as it is transmitted from the third sensor 27 to the fourth sensor 28 along the monitoring path 24. The monitoring UGW measurement is impacted by the component 14 itself and reflects how the component 14 behaves under the current environmental conditions along the monitoring path 24. Stated differently, the shape of the monitoring UGW measurement is physically impacted as it is transmitted through the component 14 and is further altered based on the current environmental conditions that the component is subjected to at the time of the measurement.

In the exemplary embodiment shown in FIG. 1, the monitoring path 24 includes a monitoring component portion 29. The monitoring component portion 29 may be a portion of the component 14 susceptible to damage, a portion of the component 14 of particular interest in regards to SHM, or a portion of the component 14 indicative of the health of the rest of the component 14. If the monitoring component portion 29 includes damage to the component 14 or some other form of structural anomaly, the monitoring UGW measurement will be impacted in a similar manner to that discussed with respect to the reference UGW measurement signals depicted in FIG. 2. For example, if the component 14 is damaged at or near the monitoring component portion 29, the monitoring UGW measurement signal may change in amplitude, the monitoring UGW measurement signal may change in the position in time, or a combination thereof.

While only the reference path 22 between the first sensor 25 and the second sensor 26 and the monitoring path 24 between the third sensor 27 and the fourth sensor 28 are depicted on the component 14, it is appreciated that additional sensors may be placed about the component 14 to allow for additional monitoring UGW measurements to be taken. Furthermore, additional monitoring UGW measurements may be taken along monitoring paths between other combinations of sensors, such as between the first sensor 25 and the fourth sensor 28. One skilled in the art will appreciate that the placement of the sensors on the component 14 and the selection of what pair of sensors to use for the monitoring UGW measurement is a design choice and contemplated by the present disclosure.

The database 30 stores a plurality of database reference UGW measurements that each correspond to at least one database monitoring UGW measurement. In a non-limiting embodiment, the database 30 is populated with the plurality of database reference UGW measurements and corresponding database monitoring UGW measurements. In a non-limiting example, the database reference UGW measurements include reference UGW measurements taken when the component 14 was subjected to varying environmental conditions. For example, the database reference UGW measurements include reference UGW measurements taken when the component 14 was subjected to different temperatures, different loading, and at different component ages. In this way, the database reference UGW measurements stored in the database 30 form a library of reference UGW measurements that represent how the component 14 behaves along the reference path 22 is varying environmental conditions.

The database monitoring UGW measurements stored in the database 30 correspond to the database reference UGW measurement. In a non-limiting embodiment, the database 30 is populated with database monitoring UGW measurements taken when the component 14 was subjected to the same environmental conditions as when the database reference UGW measurement was taken. For example, the database monitoring UGW measurements is taken along the monitoring path 24 when the component 14 is subjected to the same temperature, loading, and component age as the database reference UGW measurement. In a non-limiting embodiment, the database monitoring UGW measurement is taken at the same time as the database reference UGW measurement. In this way, the database reference UGW measurements and the database monitoring UGW measurement stored in the database 30 are related to one another in that they were taken at the same time when the component 14 is subjected to the same environmental conditions. By way of example, a database reference UGW measurement and the corresponding database monitoring UGW measurement may be taken when the component 14 has a temperature of zero degrees Celsius, when the component 14 is loaded at a maximum operational load, when the component 14 is five years old, or a combination of these factors.

In a non-limiting embodiment, a plurality of database monitoring UGW measurements taken from a plurality of monitoring paths are each associated with a single database reference UGW measurement. By way of example, the database 30 may be arranged similar to a table in which the database reference UGW measurement and the database monitoring UGW measurements are columns within the table. Each row of the table in the database 30 corresponds to database monitoring UGW measurements taken under unique environmental conditions and are associated with a single database reference UGW measurement. In this way, the database 30 includes a plurality of database reference UGW measurements that each correspond to at least one database monitoring UGW measurements.

The damage detection module 40 is in communication with the UGW device 20 and the database 30. The damage detection module 40 is configured to receive the reference UGW measurement and the monitoring UGW measurement from the UGW device 20. The damage detection module 40 is further configured to search the database 30 for the database reference UGW measurement that matches the reference UGW measurement from the UGW device 20. The damage detection module 40 searches the database 30 for the database reference UGW measurement that physically matches the reference UGW measurement. In a non-limiting example, rather than searching for the database reference UGW measurement that was taken under the same environmental conditions, the damage detection module 40 searches the database 30 and matches the physical shape of the reference UGW measurement.

When the matching database reference UGW measurement is found, the damage detection module 40 obtains the database monitoring UGW measurement that corresponds to the matched database reference UGW measurement. Since the matching database reference UGW measurement was necessarily taken under the same environmental conditions as the reference UGW measurement, the monitoring UGW measurement and the database monitoring UGW measurement were also taken under the same environmental conditions. For example, if the reference UGW measurement and the monitoring UGW measurement were taken when the component 14 has a temperature of zero degrees Celsius, then the matched database reference UGW measurement from the database 30 was also taken when the component 14 had a temperature of zero degrees Celsius. Accordingly, the database monitoring UGW measurements corresponding to the matched database reference UGW measurement were taken when the component 14 had a temperature of zero degrees Celsius.

In a non-limiting embodiment, the damage detection module 40 is further configured to compare the monitoring UGW monitoring signal with the obtained database monitoring UGW measurement. As the obtained database monitoring UGW measurement was taken under the same environmental conditions as the monitoring UGW measurement, the obtained database monitoring UGW measurement can be compared to the monitoring UGW measurement and compensate for variations due to environmental conditions. Stated differently, the database monitoring UGW measurement may be compared to the monitoring UGW measurement to remove variation due to environmental conditions of the component 14 and identify meaningful differences in the monitoring UGW measurement.

In a non-limiting embodiment, the damage detection module 40 is further configured to identify damage to the component 14 based on a comparison between the monitoring UGW measurement and the database monitoring UGW measurement. As detailed above, the damage detection module 40 uses the database 30 to obtain the database monitoring UGW measurement that was taken under the same environmental conditions as the current monitoring UGW measurement. In a non-limiting embodiment, the damage detection module 40 determines that the component 14 is damaged when the monitoring UGW measurement does not match the database monitoring UGW measurement.

The damage detection module 40 is further configured to identify damage to the component 14 based on the comparison with the database monitoring UGW measurement. As detailed above, the damage detection module 40 uses the database 30 to obtain the database monitoring UGW measurement that was taken under the same environmental conditions as the current monitoring UGW measurement. Rather than having to analyze the monitoring UGW measurement itself to determine if the monitoring component portion 29 includes damage to the component 14, the damage detection module 40 is able to identify damage to the component 14 based on the comparison with the database monitoring UGW measurement.

Alternatively, when the matching database reference UGW measurement is not found, the damage detection module 40 is configured to update the database 30 with the reference UGW measurement and the monitoring UGW measurement. In this way, the database reference UGW measurement and the database monitoring UGW measurement are updated with measurements to make a more robust and detailed database 30 of UGW measurements.

The components of the system 10 have been shown as discrete blocks in the representation of FIG. 1 to aid in understanding how the system 10 detects structural damage in a component 14 of the aircraft 12. However, one skilled in the art will appreciate that the components of the system 10 may be combined with one another in various forms without departing from the spirit of the present disclosure.

In a non-limiting embodiment, the reference path 22 on the component 14 is distant from the monitoring path 24 on the component 14. As the reference path 22 is not intended to be used to detect damage in the component 14, by keeping the reference path 22 distant from the monitoring path 24, the effect of the monitoring component portion 29 on the reference UGW measurement is minimized.

In a non-limiting embodiment, the UGW device 20 is further configured to scan the component 14 along a plurality of monitoring paths to generate a plurality of monitoring UGW measurements corresponding to the reference path 22 and a timestamp. As detailed above, while only one monitoring path 24 is depicted in FIG. 1, a plurality of monitoring paths may be scanned by the UGW device 20 to evaluate multiple monitoring component portions 29 of the component 14. Even though multiple monitoring paths are scanned to generate a plurality of monitoring UGW measurements, only one reference path 22 is needed by the damage detection module 40 to be used in searching the database 30.

In a non-limiting embodiment the UGW device 20 is further configured to scan the component 14 along the plurality of monitoring paths to generate the plurality of monitoring UGW measurements corresponding to the reference path 22 and the timestamp based upon a predetermined event. The damage detection module 40 is further configured to update the database 30 with the plurality of monitoring UGW measurements.

In a non-limiting embodiment, the predetermined event is at least one of a predetermined time period, an environmental condition, a maintenance operation, a compromising event, a scheduled evaluation, or a combination thereof. A predetermined time period may be set so that the system 10 evaluates the component 14 as often as necessary and is a design consideration. An environmental condition may be a specific component 14 temperature or temperature change, a component 14 loading or loading change, a component 14 age, or a combination thereof. A maintenance operation may trigger the system 10 to evaluate the component 14 when maintenance operation is being performed on the aircraft 12 or to provide an evaluation of the component 14 prior to performing the maintenance operation. A compromising event may be an event in which the component 14 is subjected to significant stresses outside of its normal operating range. For example, when the component 14 is exposed to loading or temperatures outside of its normal operating range. A scheduled evaluation may be a routine trigger for the system 10 to evaluate the component 14 based upon a regular occurrence, such as a take off or landing of the aircraft.

In a non-limiting embodiment, the damage detection module 40 is further configured to obtain a reference UGW measurement and a corresponding monitoring UGW measurement for each of a component condition. The damage detection module 40 is further configured to populate the database with the plurality of reference UGW measurements and corresponding monitoring UGW measurements obtained while the component is subjected to the component condition. The component condition is selected from the group including a change in temperature, a change in loading, a change in age of the component. In this way, the damage detection device 40 populates the database 30 with the data necessary for a complete and robust evaluation of the component 14.

In a non-limiting embodiment, the damage detection module 40 is further configured to filter the database 30 based on a current component condition and search the filtered database for the database reference UGW measurement that matches the reference UGW measurement. In this way, the damage detection module 40 first filters the database 30 to identify database reference UGW measurements based on a current component condition. In a non-limiting embodiment, the component condition includes a component temperature, a component loading, a component age, or a combination thereof.

In a non-limiting embodiment, the damage detection module 40 is further configured to compare the monitoring UGW measurement to a predetermined threshold value determine that damage has occurred to the component 14 based on the comparison to the threshold value. After the damage detection module 40 has obtained the monitoring UGW measurement, the threshold value is used to identify when the component 14 has been damaged.

In a non-limiting embodiment, the damage detection module 40 is further configured to compare the monitoring UGW measurement to a predetermined threshold value and the UGW device 20 is further configured to scan the component 14 along a second monitoring path to generate a second monitoring UGW measurement. The second monitoring path is proximate to the first monitoring path 24. In this way, when the damage detection module 40 suspects that there may be damage to the component 14, second monitoring path proximate to the first monitoring path 24 is used to further evaluate the health of the component 14.

It should be understood that FIG. 1 is a simplified representation of a system 10 for purposes of explanation and ease of description, and FIG. 1 is not intended to limit the application or scope of the subject matter in any way. In practice, the system 10 and/or aircraft 12 will include numerous other devices and components for providing additional functions and features, as will be appreciated in the art.

Figure 3:
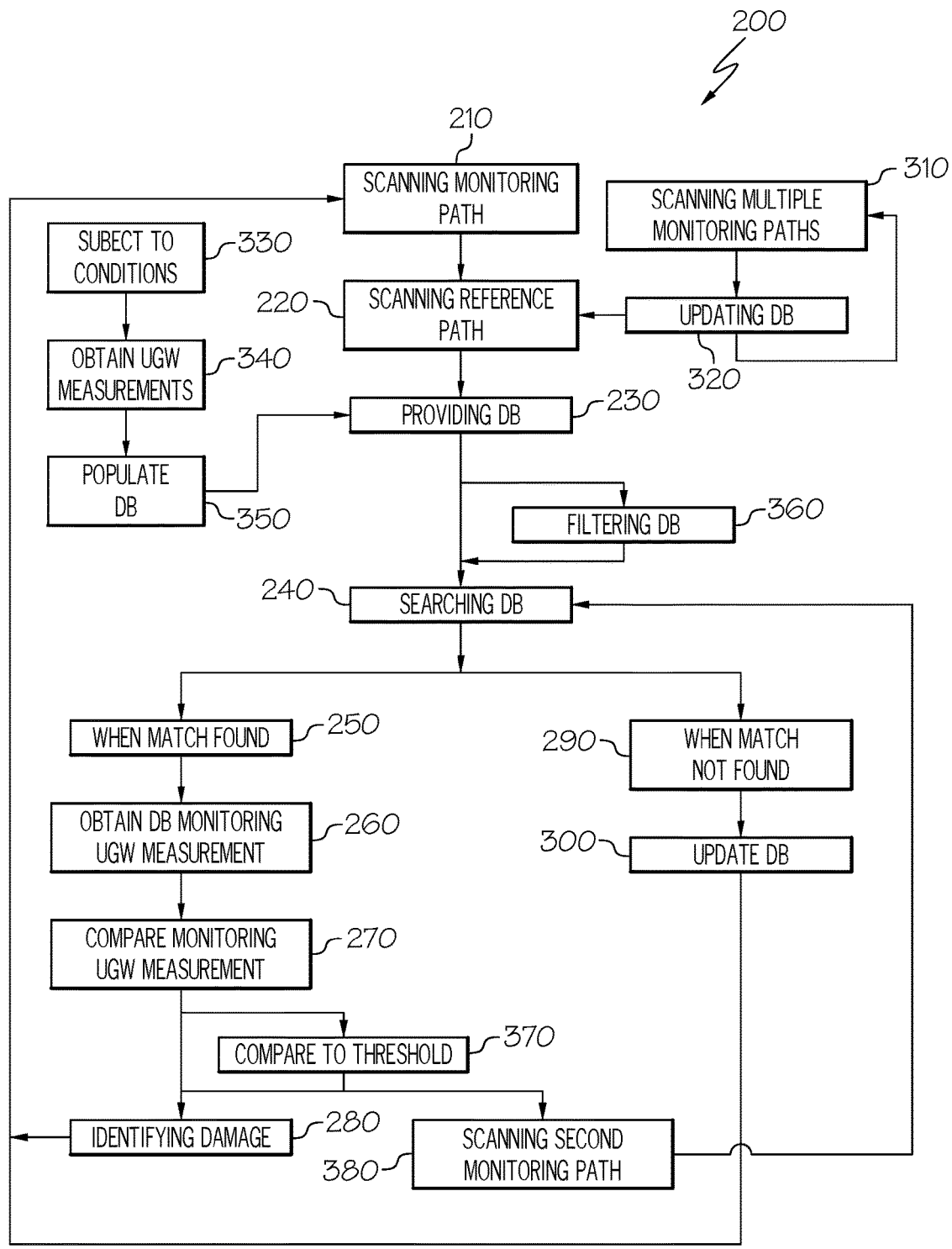
FIG. 3 is a flow diagram of an exemplary method suitable for use with the system of FIG. 1 in accordance with the exemplary embodiments.

With reference now to FIG. 3, and with continued reference to FIGS. 1 and 2, a flowchart illustrates a method 200 performed by the system 10 of FIG. 1 in accordance with the present disclosure. As can be appreciated in light of the disclosure, the order of operation within the method 200 is not limited to the sequential execution as illustrated in FIG. 2, but may be performed in one or more varying orders as applicable and in accordance with the requirements of a given application.

In various exemplary embodiments, the system 10 and method 200 are operated based on predetermined events, such as the aircraft 12 taking off from an airport or remaining stationary. Method 200 may be performed by the system 10 or may be performed by any other suitable device or system configured in a manner consistent with the teachings of the present disclosure. Unless otherwise noted, the method 200 may be performed by any of the embodiments of the system 10 previously described above.

The method 200 starts at block 210 and scans, with a UGW device, the component along a monitoring path to generate a monitoring UGW measurement. In a non-limiting embodiment, the UGW device 20 scans the component 14 along the monitoring path 24 to generate the monitoring UGW measurement. At block 220, the method 200 scans with the UGW device, the component along a reference path to generate a reference UGW measurement, the reference path corresponding to the monitoring path. In a non-limiting embodiment, the UGW device 20 scans the component 14 along the reference path 22 to generate the reference UGW measurement.

At block 230, the method 200 provides a database having a plurality of database reference UGW measurements each corresponding to a database monitoring UGW measurement. In a non-limiting embodiment, the database 30 has the plurality of database reference UGW measurements each corresponding to a database monitoring UGW measurement. At block 240, the method 200 searches the database for the database reference UGW measurement that matches the reference UGW measurement. In a non-limiting embodiment, the damage detection module 40 searches the database 30 for the database reference UGW measurement that matches the reference UGW measurement.

At block 250, the method 200 finds the matching database reference UGW measurement and proceeds to 260. At block 260, the method 200 obtains from the database the database monitoring UGW measurement that corresponds to the matched database reference UGW measurement. In a non-limiting embodiment, the damage detection module 40 obtains from the database 30 the database the database monitoring UGW measurement that corresponds to the matched database reference UGW measurement.

At block 270, the method 200 compares the monitoring UGW measurement with the obtained database monitoring UGW measurement. In a non-limiting embodiment, damage detection module 40 compares the monitoring UGW measurement with the obtained database monitoring UGW measurement. At block 280, the method identifies damage to the component based the comparison with the database monitoring UGW measurement. In a non-limiting embodiment, damage detection module 40 identifies damage to the component 14 based on the comparison with the database monitoring UGW measurement. From block 280, the method 200 returns to block 210 and scans the monitoring path.

Following 240, when the method 200 does not find the matching database reference UGW measurement, the method 200 proceeds to 290 and 300. At 300, the method 200 updates the database with the reference UGW measurement and the monitoring UGW measurement. In a non-limiting embodiment, the damage detection module 40 updates the database 30 with the reference UGW measurement and the monitoring UGW measurement. Following 300, the method 200 returns to block 210 and scans the monitoring path. In this way, the method 200 detects structural damage in a component.

In a non-limiting embodiment of the method 200, the reference path on the component is distant from the monitoring path on the component. In a non-limiting embodiment, the reference path 22 on the component 14 is distant from the monitoring path 24 on the component.

In a non-limiting embodiment, the method 200 further includes block 310 and scans, with the UGW device, the component along a plurality of monitoring paths to generate a plurality of monitoring UGW measurements corresponding to the reference path and a timestamp. In a non-limiting embodiment, the UGW device 20 scans the component 14 along a plurality of monitoring paths to generate a plurality of monitoring UGW measurements corresponding to the reference path 22 and a timestamp. At block 320, the method 200 updates the database with the plurality of monitoring UGW measurements. In a non-limiting embodiment, the damage detection module 40 updates the database 30 with the plurality of monitoring UGW measurements. Following block 320, the method proceeds to 220 and scans the reference path.

In a non-limiting embodiment, following 320, the method 200 returns to 310 and re-scans the component along the plurality of monitoring paths to generate the plurality of monitoring UGW measurements corresponding to the reference path and the timestamp based on a predetermined event. In a non-limiting embodiment, the UGW device 20 scans the component 14 along the plurality of monitoring paths to generate the plurality of monitoring UGW measurements corresponding to the reference path 22 and the timestamp based on a predetermined event. In a non-limiting embodiment, the predetermined event is selected from the group consisting of a predetermined time period, an environmental condition, a maintenance operation, a compromising event, a scheduled evaluation, or a combination thereof.

In a non-limiting embodiment, the method 200 includes block 330 and subjects the component to a plurality of component conditions. At 340, the method 200 obtains a reference UGW measurement and a corresponding monitoring UGW measurement for each of the component conditions. In a non-limiting embodiment, the damage detection module 40 obtains the reference UGW measurement and the corresponding monitoring UGW measurement for each of the component conditions. At 350, the method 200 populates the database with the plurality of database reference UGW measurements and corresponding database monitoring UGW measurements obtained while subjecting the component the component conditions. In a non-limiting embodiment, the damage detection module 40 populates the database 30 with the plurality of database reference UGW measurements and corresponding database monitoring UGW measurements obtained while subjecting the component 14 to the component conditions. In a non-limiting embodiment, the component conditions are selected from the group including a change in temperature, a change in loading, a change in age of the component, or combinations thereof.

In a non-limiting embodiment, the method 200 includes block 360 and filters the database based on a current component condition. In a non-limiting embodiment, the damage detection module 40 filters the database 30 based on a current component condition. Following 360, the method 200 proceeds to 240 and searches the filtered database.

In a non-limiting embodiment, the method 200 includes block 370 and compares the monitoring UGW measurement to a predetermined threshold. In a non-limiting embodiment, the damage detection module 40 compares the monitoring UGW measurement to a predetermined threshold. Following 370, the method 200 proceeds to 280 and identifies damage to the component based on the comparison to the threshold value.

In a non-limiting embodiment, the method 200 includes block 380 and scans, with the UGW device, the component along a second monitoring path to generate a second monitoring UGW measurement. In a non-limiting embodiment, the UGW device 20 scans the component 14 along a second monitoring path to generate a second monitoring UGW measurement. Following 380, the method 200 proceeds to 240 and searches the database. In a non-limiting embodiment, the second monitoring path is proximate to the first monitoring path.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A system for detecting structural damage in a component, the system comprising:
   an ultrasonic guided wave (UGW) device configured to scan the component by transmitting an ultrasonic signal from a first structural monitoring sensor located on the component to a second structural monitoring sensor located on the component along a structural monitoring path located between the first structural monitoring sensor and the second structural monitoring sensor in order to generate a current structural monitoring UGW measurement for a monitoring portion along the structural monitoring path that is subject to structural health monitoring (SHM), and further configured to simultaneously scan the component by transmitting an ultrasonic signal from a first environmental reference sensor located on the component to a second environmental reference sensor located on the component along a reference path located between the first environmental reference sensor and the second environmental reference sensor in order to generate a current environmental reference UGW measurement for use as a reference in comparison to the current structural monitoring UGW measurement, where the current structural monitoring UGW measurement and the current environmental reference UGW measurement are generated under identical environmental conditions;

a database having a plurality of historic environmental reference UGW measurements of the component, each corresponding to a historic structural monitoring UGW measurement of the component, where each historic environmental reference UGW measurement of the component and the corresponding historic structural monitoring UGW measurement of the component were generated under identical environment conditions; and a damage detection module configured to search the database for the historic environmental reference UGW measurement of the component that matches the current environmental reference UGW measurement, wherein, when the matched historic environmental reference UGW measurement of the component is found, the damage detection module is configured to:
  obtain, from the database, the historic structural monitoring UGW measurement of the component corresponding to the matched historic environmental reference UGW measurement of the component,
  compare the current structural monitoring UGW measurement with the obtained historic structural monitoring UGW measurement of the component, and
  identify damage to the component based on the comparison between the current structural monitoring UGW measurement and the historic structural monitoring UGW measurement of the component, where the damage detection module compensates for any impact of environmental conditions on the current structural monitoring UGW measurement by referencing the historic structural monitoring UGW measurement of the component which was generated under identical environmental conditions, when the matched historic environmental reference UGW measurement of the component is not found, the damage detection module is configured to:
  update the database with the current environmental reference UGW measurement and the current structural monitoring UGW measurement.

2. The system of claim 1 where the environmental conditions comprise temperature.

3. The system of claim 1 wherein the UGW device is further configured to:
  scan the component along a plurality of structural monitoring paths to generate a plurality of current structural monitoring UGW measurements corresponding to the environmental reference path and a timestamp.

4. The system of claim 3 wherein,
  the UGW device is further configured to re-scan the component along the plurality of structural monitoring paths to generate the plurality of current structural monitoring UGW measurements corresponding to the environmental reference path and the timestamp based upon a predetermined event, and
  the damage detection module is further configured to update the database with the plurality of current structural monitoring UGW measurements.

5. The system of claim 4 wherein the predetermined event is selected from the group consisting of: a predetermined time period, an environmental condition, a maintenance operation, a compromising event, a scheduled evaluation, or a combination thereof.

6. The system of claim 1 wherein the damage detection module is further configured to:
  obtain a plurality of component condition environmental reference UGW measurements and a corresponding plurality of component condition structural monitoring UGW measurements for each of a component condition, where the component condition structural monitoring UGW measurements and the corresponding component condition environmental reference UGW measurements are obtained under identical environmental conditions; and
  populate the database with the plurality of component condition environmental reference UGW measurements and corresponding component condition structural monitoring UGW measurements obtained while the component is subjected to the component condition,
  wherein the component condition is selected from the group including a change in temperature, a change in loading, a change in age of the component, or combinations thereof.

7. The system of claim 6 wherein the damage detection module is further configured to:
  filter the database based on a current component condition; and
  search the filtered database for the historic component condition environmental reference UGW measurement that matches the current component condition environmental reference UGW measurement.

8. The system of claim 1, wherein the damage detection module is further configured to:
  compare the current structural monitoring UGW measurement to a predetermined threshold value; and
  determine that damage has occurred to the component based on the comparison to the threshold value.

9. The system of claim 1, wherein,
  the damage detection module is further configured to compare the current structural monitoring UGW measurement to a predetermined threshold value, and
  the UGW device is further configured to scan the component along a second monitoring path to generate a second current structural monitoring UGW measurement, the second monitoring path being proximate to the first monitoring path.

10. A method for detecting structural damage in a component, the method comprising:
  scanning, with an ultrasonic guided wave (UGW) device by transmitting an ultrasonic signal from a first structural monitoring sensor located on the component to a second structural monitoring sensor located on the component, the component along a monitoring path located between the first structural monitoring sensor and the second structural monitoring sensor in order to generate a current structural monitoring UGW measurement for a monitoring portion along the structural monitoring path that is subject to structural health monitoring (SHM);
  scanning, with the UGW device by transmitting an ultrasonic signal from a first environmental reference sensor located on the component to a second environmental reference sensor located on the component, the component along a reference path located between the first environmental reference sensor and the second environmental reference sensor in order to generate a current environmental reference UGW measurement for use as a reference in comparison to the current structural monitoring UGW measurement, the reference path corresponding to the monitoring path, where the current structural monitoring UGW measurement and the current environmental reference UGW measurement are generated under identical environmental conditions;

providing a database having a plurality of historic environmental reference UGW measurements of the component, each corresponding to a historic structural monitoring UGW measurement of the component;

searching the database for the historic environmental reference UGW measurement of the component that matches the current environmental reference UGW measurement; and when the matched historic environmental reference UGW measurement of the component is found:
  obtaining, from the database, the historic structural monitoring UGW measurement of the component corresponding to the matched historic environmental reference UGW measurement of the component;
  comparing the current structural monitoring UGW measurement with the obtained historic structural monitoring UGW measurement of the component,
  identifying damage to the component based on the comparison between the current structural monitoring UGW measurement and the historic structural monitoring UGW measurement of the component, and
  compensating for any impact of environmental conditions on the current structural monitoring UGW measurement by referencing the historic structural monitoring UGW measurement of the component which was generated under identical environmental conditions,
  when the matched historic environmental reference UGW measurement of the component is not found,
  updating the database with the current environmental reference UGW measurement and the current structural monitoring UGW measurement.

11. The method of claim 10, where the environmental conditions comprise temperature.

12. The method of claim 10 further comprising:
scanning, with the UGW device, the component along a plurality of structural monitoring paths to generate a plurality of current structural monitoring UGW measurements corresponding to the environmental reference path and a timestamp; and
updating the database with the plurality of current structural monitoring UGW measurements.

13. The method of claim 12 further comprising:
re-scanning, with the UGW device, the component along the plurality of structural monitoring paths to generate the plurality of current structural monitoring UGW measurements corresponding to the environmental reference path and the timestamp based upon a predetermined event; and
updating the database with the plurality of current structural monitoring UGW measurements.

14. The method of claim 13, wherein the predetermined event is selected from the group consisting of: a predetermined time period, an environmental condition, a maintenance operation, a compromising event, a scheduled evaluation, or a combination thereof.

15. The method of claim 10 further comprising:
subjecting the component to a plurality of component conditions;
obtaining a plurality of component condition environmental reference UGW measurements and a corresponding plurality of component condition structural monitoring UGW measurements for each of the component conditions, where the structural monitoring UGW measurements and the corresponding environmental reference UGW measurements are obtained under identical environmental conditions; and
populating the database with the plurality of component condition environmental reference UGW measurements and corresponding plurality of component condition structural monitoring UGW measurements obtained while subjecting the component to the component conditions.

16. The method of claim 15, wherein the component conditions are selected from the group including a change in temperature, a change in loading, a change in age of the component, or combinations thereof.

17. The method of claim 15, further comprising:
filtering the database based on a current component condition; and
searching the filtered database for the historic component condition environmental reference UGW measurement that matches the current component condition environmental reference UGW measurement.

18. The method of claim 10, further comprising:
comparing the current structural monitoring UGW measurement to a predetermined threshold value; and
determining that damage has occurred to the component based on the comparison to the threshold value.

19. The method of claim 10, further comprising:
comparing the current structural monitoring UGW measurement to a predetermined threshold value; and
scanning, with the UGW device, the component along a second monitoring path to generate a second current structural monitoring UGW measurement.

20. The method of claim 19, wherein the second monitoring path is proximate to the first monitoring path.

* * * * *